United States Patent [19]

Chang et al.

[11] Patent Number: 4,824,777

[45] Date of Patent: Apr. 25, 1989

[54] METHOD FOR DETERMINING THYROXINE UPTAKE

[75] Inventors: Steve C. S. Chang, Franklin; Thomas E. Miller, Norwood; Elizabeth K. Krodel, Arlington, all of Mass.

[73] Assignee: Ciba Corning Diagnostics Corp., Medfield, Mass.

[21] Appl. No.: 71,661

[22] Filed: Jul. 8, 1987

[51] Int. Cl.$^4$ .................. G01N 33/53; G01N 33/546; G01N 33/543; G01N 33/533

[52] U.S. Cl. ........................................ 435/7; 436/500; 436/518; 436/523; 436/525; 436/526; 436/527; 436/529; 436/534; 436/546; 436/811; 436/817

[58] Field of Search .................... 435/7; 436/500, 523, 436/545, 546, 526, 817, 518, 525, 527, 533, 534, 536, 532, 538, 530, 529, 811, 823

[56] References Cited

U.S. PATENT DOCUMENTS

| | | | |
|---|---|---|---|
| 4,032,626 | 6/1977 | Ward | 436/500 |
| 4,347,059 | 8/1982 | Polito et al. | 436/500 |
| 4,476,228 | 10/1984 | Huchzermeier et al. | 436/500 |
| 4,554,088 | 11/1985 | Whitehead et al. | 436/526 |
| 4,591,569 | 5/1986 | Wagner et al. | 436/817 |

FOREIGN PATENT DOCUMENTS

| | | | |
|---|---|---|---|
| 0171871 | 2/1986 | European Pat. Off. | 436/548 |
| 0190765 | 8/1986 | European Pat. Off. | 435/7 |

OTHER PUBLICATIONS

Gupta et al., American Journal of Clinical Phathology, vol. 79, No. 3, Mar. 1983, pp. 334–340.
Weeks et al., Clin. Chem. vol. 29, 1983, pp. 1474–1479.
Amino et al., Clinical Chemistry, vol. 29, No.2, pp. 321–325, 1983.

*Primary Examiner*—Robert J. Warden
*Assistant Examiner*—Florina B. Hoffer
*Attorney, Agent, or Firm*—Daniel Reitenbach

[57] ABSTRACT

A method for determining thyroxine uptake of a sample serum comprising: (a) incubating the sample serum with solid phase thyroxine and labeled anti-TBG antibody; (b) separating the solid phase from the unbound labeled antibody; (c) measuring the amount of label associated with the solid phase; and (d) calculating the thyroxide uptake ratio of the sample serum by relating the measurement of step (c) to a measurement of a reference serum.

12 Claims, No Drawings

METHOD FOR DETERMINING THYROXINE UPTAKE

FIELD OF THE INVENTION

This invention relates to a method for determining thyroxine uptake of a sample serum using solid-phase thyroxine ($T_4$) and labeled anti-TBG antibody.

BACKGROUND OF THE INVENTION

Thyroxine binding globulin (TBG) is the principal serum carrier protein for thyroxine ($T_4$) and triiodothyronine ($T_3$). The physiological role of TBG is best understood in the context of $T_4$ transport and metabolism. Immediately after $T_4$ is released into circulation, it is nearly completely bound to the three thyroxine binding proteins: albumin, prealbumin, and principally, TBG. The unbound fraction of $T_4$ (free $T_4$) provides an accurate assessment of the thyrometabolic status of a patient. The concentration of free $T_4$ is a function of both total serum $T_4$ and $T_4$ binding protein concentrations. Of the three binding proteins, variation in the TBG concentration will affect the total $T_4$ concentration the most.

Unsaturated TBG levels and a free $T_4$ index (FTI) are often used as indicators of thyroid status. FTI is conventionally obtained by calculating the product of total $T_4$ and a $T_3$ uptake test. Total $T_4$ can be determined by competitive protein binding, displacement analysis, or radioimmunoassay. The method of choice for estimating unsaturated TBG levels has been the $T_3$ uptake test.

In the $T_3$ uptake test, an equilibrium is developed between the patient's serum, added labeled $T_3$, and an inert exogeneous binder (separating agent) of the labeled $T_3$. One must add a sufficient amount of labeled $T_3$ to saturate the binding sites on the TBG after which the labeled $T_3$ that is unbound is adsorbed by the separating agent and counted. Therefore, when the endogeneous thyroxine level is increased, as in hyperthyroidism, serum TBG is relatively saturated and the $T_3$ uptake will be high. Conversely, in the hypothyroid state, where thyroxine output is low, the labeled exogeneous $T_3$ will bind to the relatively unsaturated TBG yielding a low $T_3$ uptake.

The major variations in $T_3$ uptake methodology have been centered around the chemical nature of the separating agent. Ion exchange resins, hemoglobin saturated charcoal, Sephadex G-25, nylon, inorganic crystalline materials, $T_3$ antibody immobilized on the walls of polymer-coated test tubes or particles and $T_3$ antibody immobilized on certain resins, for example, all have been used as inert binders of labeled $T_3$. See, generally, U.S. Pat. No. 4,225,412.

U.S. Pat. No. 4,032,626 describes a process for determining the concentration of TBG in a fluid sample using radiolabeled $T_4$ and anti-TBG antibodies immobilized on insoluble support materials. The sample is incubated with the labeled $T_4$ and the immobilized anti-TBG antibodies. The concentration of TBG can be determined by separating the labeled composite from the unbound labeled $T_4$ and counting the bound labeled $T_4$.

It is the purpose of this invention to provide a novel method for determining thyroxine uptake of a sample serum for use in determining the level of unsaturated TBG and free thyroxine index of the sample serum.

DESCRIPTION OF THE INVENTION

This invention relates to a method for determining thyroxine uptake (TU) of a sample serum comprising the steps of:
(a) incubating the sample serum with (i) a composite comprising thyroxine ($T_4$) immobilized on an insoluble carrier material and (ii) an excess of a labeled antibody to TBG (anti-TBG) over endogenous TBG, to form a complexed composite,
(b) separating the complexed composite from unbound labeled antibody;
(c) measuring the amount of label associated with the complexed composite; and
(d) relating the measurement of step (c) to a measurement of a reference serum to determine a thyroxine uptake ratio of the sample serum.

The $T_4$ can be immobilized on the insoluble carrier material by any procedure which produces an immobilized $T_4$ capable of being bound by TBG. For example, the procedure described by Kägedal et al. in Clinica Chimica Acta 78, pp. 103–111 (1977) (hereinafter Kagedal et al.), utilizing a bifunctional reagent, is useful in immobilizing the $T_4$ for the purpose of this invention.

The insoluble carrier material can be any of the known support materials such as cellulose, Sephadex, polystyrene, nylon, polyacrylamide, latex, glass, magnetizable particles like iron oxide particles, etc. Preferably, $T_4$ is immobilized onto a high surface area, insoluble carrier material, in particulate form, having an average particle size (e.g. 0.01 to 10 microns) that limits gravimetric settling over the time of incubation. The particle size should preferably be large enough to enable easy and rapid separation using available laboratory procedures.

Paramagnetic particles are a preferred carrier material. These particles comprise a ferric oxide core surrounded by a polymerized silane coating (see, e.g., U.S. Pat. No. 4,554,088). $T_4$ can be immobilized onto the surface of the particles by first immobilizing a glycoprotein (such as $\alpha$,-acid glycoprotein or mucin) on the particles and then immobilizing the $T_4$ on the glycoprotein with a bifunctional epoxide (see Kägedal et al.).

The amount of immobilized $T_4$ per unit sample serum can vary but must be such that the capacity for TBG binding is sufficient to discriminate the physiological range of free TBG in clinical samples. Normal human serum contains from about 15 $\mu g$ to about 34 $\mu g$ TBG per ml of serum and in pathological states, the amount can vary from less than 10 $\mu g$ to about 60 $\mu g$ TBG per ml of serum. The amount of immobilized $T_4$ necessary can be determined empirically using known methods of titrating the immobilized $T_4$ against samples with varying known amounts of free TBG. This titration will determine the amount of immobilized $T_4$ necessary to distinguish the low end of the physiologial range of free TBG from the upper end of the physiological range of free TBG. Preferably, about 0.1 to 1.0 $\mu g$, more preferably, about 0.5 $\mu g$, of $T_4$ immobilized on the carrier material per 10 $\mu l$ of serum sample is utilized.

The amount of $T_4$ immobilized on a particle can vary depending upon preparation conditions. As a practical matter, therefore, the amount of immobilized $T_4$ in a sample will be adjusted by increasing or decreasing the amount of particles in the sample.

Unlabeled anti-TBG antibody can be prepared utilizing known methods for preparing monoclonal antibodies (see, e.g., G. Kohler and C. Milstein, Eur. J. Immunology, vol. 6, 511-519, 1976). The anti-TBG antibody is then purified and labeled by known means (e.g., with enzymatic, fluorogenic, radiometric, bioluminescent, chemiluminescent, etc., labels and markers) (see, e.g., Woodhead et al., Clinical Chemistry 29(8), pp. 1474–1479, 1983). Preferably, the anti-TBG antibody is labeled with an acridinium ester. Any suitable acridinium ester can be used in the method of this invention. Useful acridinium esters are disclosed in copending U.S. Application Ser. No. 915,527, filed on Oct. 6, 1986, herein incorporated by reference. Particularly preferred is 2′, 6′-dimethyl-4′-(N-succinimidyloxycarbonyl)phenylacridine-9-carboxylate.

There should be an excess of labeled anti-TBG antibody compared to immobilized TBG. The amount of anti-TBG antibody necessary can be determined empirically using known methods of titrating the anti-TBG antibody against samples of varying known amounts of TBG. This tritration will determine the amount of anti-TBG antibody necessary to discriminate TBG at the levels commonly encountered in clinical samples. The excess of anti-TBG antibody is necessary so that the uptake of labeled anti-TBG is directly related to the amount of TBG bound on the complexed composite. Preferably, about 10 ng to about 100 ng, more preferably, about 50 ng, of labeled anti-TBG antibody per 10 μl of sample serum is utilized.

The incubation conditions can vary, depending on time, temperature, and final incubation volume, but, preferably, the incubation should be conducted for at least 15 minutes at room temperature.

After the incubation, the complexed composite is separated from the incubation medium. The composite is formed on a water-insoluble solid phase which can be separated by conventional means such as sedimentation, centrifugation or magnetism depending on the insoluble carrier material used. In the preferred embodiment wherein the carrier material are magnetizable particles, separation is preferably conducted by placing the particles in a magnetic field.

The uptake of labeled anti-TBG antibody is directly related to the amount of TBG complexed on the complexed composite. The amount of label associated with the complexed composite can be determined by at least two methods: (1) direct quantitation of the label associated with the complexed composite, or (2) indirect quantitation of the label remaining in the incubation medium after separation and then subtracting this amount from the total label offered. The suitable quantitation procedure will depend largely on the label used. For example, when the label used is acridinium ester, direct quantitation of the label associated with the complexed composite is the preferred method and can be determined in a luminometer by measuring the photons released by the chemiluminescent reaction of the acridinium ester. The signal produced by the photons is measured in relative light units (RLU), which quantitate the light emitted from the oxidation of the acridinium ester label on the anti-TBG antibody.

The amount of label determined to be associated with the complexed composite in the method of this invention is converted to a thyroxine uptake (T-uptake) ratio by dividing the signal from a reference serum (such as normal human serum) by the signal from the sample serum test, i.e.:

$$T\text{-uptake ratio} = \frac{\text{signal from reference serum}}{\text{signal from sample serum}}$$

The signal generated from the reference serum is obtained using the same label, procedure and reaction conditions that are used to obtain the signal from the sample serum.

It the T-uptake is 1, then the level of unsaturated TBG in the sample serum is the same as the level of unsaturated TBG in the reference serum. If the T-uptake ratio is less than 1, then the level of unsaturated TBG in the sample serum is higher than the level of unsaturated TBG in the reference serum. If the T-uptake ratio is greater than 1, then the level of unsaturated TBG in the sample serum is lower than the level of unsaturated TBG in the reference serum.

This T-uptake ratio can then be used to calculate the free thyroxine index of the sample using the following equation:

$$\text{Total } T_4 \times \frac{\text{T-uptake ratio}}{100} = FTI$$

Total $T_4$ can be determined using any known procedure in the art such as, for example, by utilizing a MAGIC $T_4$ Radioimmunoassay Kit (Ciba Corning Diagnostics Corp., Medfield, Mass.).

The following examples illustrate the method of this invention.

EXAMPLE 1

A. Paramagnetic particles were obtained from Advanced Magnetics, Inc. (Cambridge, Mass.).

250 mg of the particles were placed in a conical centrifuge tube and washed 5 times with 25 ml volumes of water. 25 ml of a solution of 2.5% glutaraldehyde in 10 mM acetate buffer, pH5.5, was then added to the tube and the contents of the tube were then mixed gently at room temperature for 3 hours. The tube was placed in a magnetic field to separate the particles from the glutaraldehyde solution and then the glutaraldehyde solution was decanted. The particles were then washed once with 25 ml of 10 mM acetate buffer, pH5.5. 25 ml of a 5 mg/ml solution of $\alpha$,-1-acid glycoprotein in 10 mM acetate buffer, pH5.5, were then added to the tube and the contents of the tube were then mixed gently overnight at room temperature. The particles were separated out in a magnetic field and the supernatant decanted. The particles were washed 4 times in 25 ml volume of water. To the tube was added 20 ml of 30 mM sodium phosphate buffer, pH7.4 and 20 μl of 1,4-butanediol diglycidyl ether, and the contents of the tube were then mixed gently overnight at room temperature. The particles were separated out in a magnetic field and the supernatant decanted. The particles were than washed 5 times with 25ml volumes of water.

The following $T_4$ solution was prepared:
40 ml of 50 mM sodium bicarbonate, pH9.5
10 μl dimethylformamide
1 ml of 20 mg/μl solution of $T_4$ in 0.1N NaOH.

The $T_4$ solution was added to the tube containing the particles and the contents of the tube were then mixed gently overnight at room temperature. The tube was placed in a magnetic field to separate the particles from the $T_4$ solution and the $T_4$ solution was decanted. The particles were washed 5 times with 25 ml volumes of water. A 25 ml solution of 2M glycine in 50 mM bicarbonate buffer was added to the tube and the contents of the tube were then mixed gently overnight at room temperature. The particles were magnetically separated, the glycine buffer decanted and the particles were then washed 3 times with 25 ml volumes of water. A 25 ml solution of 2.5% bovine serum albumin (BSA) in 10 mM phosphate buffered silane, pH7.4, was added to the tube and the contents of the tube were then mixed gently overnight at room temperature. The particles were magnetically separated, the BSA solution decanted and then the particles were washed 3 times with 25 ml volume of water. The resulting particles were then resuspended in 10 mM sodium phosphate buffer to a final concentration of 10 mg/ml.

B. Ascitic fluid containing anti-human TBG antibody was obtained from Meloy Laboratories (Springfield, Va.). The monoclonal antibody was purified from the ascitic fluid by the following procedure using an Affi-gel Protein A MAPS II Kit (Bio-Rad Laboratories, Richmond, Calif.).

0.1 ml of the ascitic fluid was diluted with 0.1 ml of the Binding Buffer from the Affi-gel Protein A MAPS II Kit. The diluted ascitic fluid was then mixed with 1 ml of the Protein-A gel suspension from the Affi-gel Protein A MAPS II Kit prewashed with the Binding Buffer. This gel mixture was then packed in a 1×5 cm column and washed with 15× bed volume of the gel mixture with Binding Buffer. The anti-human TBG antibody was eluted from the gel mixture using the Eluting Buffer from the Affi-gel Protein A MAPS II Kit at pH6.0. The elution was monitored at a wavelength of 280Å to determine the point of elution of the antibody. The antibody was then separated from the Elution Buffer by dialysis against PBS buffer.

The anti-human TBG antibody was labeled with acridinium ester using the procedure described in Woodhead, et al, Clincial Chemistry 29(8), 1474–1479 (1983), using 2′, 6′-dimethyl-4′-(N-succinimidyloxycarbonyl)phenyl acridine-9-carboxylate as the starting acridinium ester. The procedure utilized was as follows:

250 μg of the antibody was diluted in 1 ml of a 0.1M sodium phosphate buffer/0.15M NaCl, pH8.0, solution. 20 μg of the acridinium ester was diluted in 200 μl of dimethylformamide. The diluted acridinium ester was added to the diluted antibody solution and allowed to react for 15 minutes at room temperature. 0.5 ml of a 10 mg/ml lysine solution was then added to the acridinium ester-antibody reaction mixture and the reaction mixture was then passed through a 2×20 cm Sephadex G-100 (Pharmacia Ltd, Uppsala, Sweden) column. The labeled antibody was eluted using the Elution Buffer. The eluent was monitored at a wavelength of 280Å. Labeled antibody came out in the void volume.

C. Reference serum was prepared from normal human serum by removing lipids and adjusting electrolytes according to the following procedure:

Pooled human serum was treated with Aerosil 380 (available from Degussa Corp., Peterboro, N.J.) (20 g/l liter of serum) by adsorption to remove lipid. The serum was then passed through a 0.22 micron membrane filter. The pH of the serum was then adjusted to between 7.45 and 7.55 with dilute HCl or NaOH.

D. A series of serum samples containing decreasing amounts of free TBG (see Table 1) were prepared as follows: A pool of human serum is depleted of $T_4$ hormones by first adjusting the pH of the serum to 10.5 with 10N NaOH and then filtering the serum through a 0.22 micron membrane filter. The serum is then pumped and recycled through Dowex 1×2 anion exchange resin several times to remove $T_4$. The serum was then adjusted to pH 7.35–7.45 with 10N HCl. The TBG in this $T_4$-depleted preparation was completely unsaturated. Total TBG concentrations were determined by radioimmunoassay using an IMMOPHASE TBG Radioimmunoassay Kit (Ciba Corning Diagnostics Corp., Medfield, Mass.). Known amounts of $T_4$ was added to this serum preparation and a series of serum samples containing TBG at varying levels of saturation were prepared (see Table 1).

Each sample was measured for $T_4$ and total TBG using the conventional radioimmunoassay procedures described above. The $T_3$-uptake ratio of each sample was determined using a conventional radioimmunoassay (MAGIC $T_3$-Uptake, Ciba Corning Diagnostics Corp., Medfield, MA). The T-uptake ratio for each sample was determined using the following procedure:

To a test tube containing 500 μl of a suspension of the $T_4$ paramagnetic particles (100μg/ml) prepared in A was added 10 μl of each sample and 100 μl of a solution of the acridinium ester labeled anti-human TBG antibody prepared in B (150ng/ml). The resulting suspension was incubated for 15 minutes at room temperature. The suspension was then placed in a magnetic field by placing the test tube in a specially designed rack useful for magnetic separation of paramagnetic particles in test tubes (available from Ciba Corning Diagnostics Corp., Medfield, MA). The magnetic field separated the particles from the remainder of the suspension and the supernatant was then decanted. The particles were washed once in 50 μl of water, magnetically separated and the water decanted. 0.3 ml of a solution of 0.1% hydrogen peroxide in 0.1N $HNO_3$ was added to the tube and the light emission triggered by the injection of 0.3 ml of 0.25N NaOH containing detergent was detected in a luminometer (Photon Counter, Laboratorium Berthold, Wildbad, West Germany). The light emitted was recorded as relative light units (RLU). RLU was converted to T-uptake ratio using the following equation:

$$T\text{-Uptake ratio} = \frac{RLU \text{ of reference serum}}{RLU \text{ of sample serum}}$$

The radiometric signal emitted for each sample tested using the MAGIC $T_3$-Uptake radioimmunoassay was detected in a scintillation counter and recorded as counts per minute (CPM) (see Table 1). CPM was converted to $T_3$-uptake ratio using the following equation:

$$T_3\text{-uptake ratio} = \frac{CPM \text{ of reference serum}}{CPM \text{ of sample serum}}$$

TABLE 1

Comparison of T-Uptake method and $T_3$-Uptake method

| Sample | $T_4$ (μg/dl) | TBG (μg/dl) | RLU | T-uptake ratio | CPM | $T_3$-uptake ratio |
|---|---|---|---|---|---|---|
| Reference serum | | | 218,000 | 1 | 13514 | 1 |
| 1. | 0 | 16.9 | 215,835 | 1.01 | 14585 | 1.08 |
| 2. | 2.5 | 16.7 | 189,585 | 1.15 | 14372 | 1.06 |
| 3. | 5 | 17.9 | 178,780 | 1.22 | 16329 | 1.21 |
| 4. | 10 | 15.6 | 147,195 | 1.49 | 17889 | 1.32 |
| 5. | 15 | 15.7 | 129,735 | 1.68 | 19263 | 1.43 |
| 6. | 30 | 14.7 | 106,570 | 2.06 | 21876 | 1.62 |

EXAMPLE 2

Using the procedure described in Example 1D for determining T$_3$-Uptake and T-Uptake, serum from 20 patients were measured. The results are listed in Table 2 below.

TABLE 2

Comparison of T-Uptake Method and T$_3$-Uptake Method Using Serum From Different Patients

| Sample number | RLU | T-Uptake Ratio | CPM | T$_3$ Uptake Ratio |
|---|---|---|---|---|
| Reference serum | 207,598 | 1 | 9227 | 1 |
| 1 | 127,240 | 1.63 | 11408 | 1.48 |
| 2 | 157,320 | 1.32 | 9923 | 1.08 |
| 3 | 139,323 | 1.47 | 10107 | 1.1 |
| 4 | 136,676 | 1.52 | 10968 | 1.19 |
| 5 | 169,263 | 1.23 | 9830 | 1.07 |
| 6 | 177,286 | 1.17 | 8603 | 0.93 |
| 7 | 240,840 | 0.86 | 6321 | 0.69 |
| 8 | 189,773 | 1.09 | 8137 | 0.88 |
| 9 | 162,603 | 1.28 | 9354 | 1.01 |
| 10 | 188,520 | 1.1 | 8342 | 0.9 |
| 11 | 262,7361 | 0.79 | 6764 | 0.73 |
| 12 | 209,016 | 0.99 | 8079 | 0.88 |
| 13 | 239,833 | 0.87 | 6586 | 0.71 |
| 14 | 182,780 | 1.14 | 10501 | 1.14 |
| 15 | 257,226 | 0.81 | 6848 | 0.74 |
| 16 | 204,626 | 1.01 | 7469 | 0.81 |
| 17 | 287,713 | 0.72 | 5458 | 0.59 |
| 18 | 187,900 | 1.1 | 8994 | 0.97 |
| 19 | 151,956 | 1.37 | 11600 | 1.26 |
| 20 | 179,103 | 1.16 | 9063 | 0.98 |

As can be seen from Examples 1 and 2, there is an excellent correlation between the art-recognized T$_3$-Uptake method and the method of this invention.

What is claimed is:

1. A method for determining the thyroxine uptake of a sample serum comprising the steps of:
   (a) incubating the sample serum with (i) a composite comprising thyroxine immobilized on an insoluble carrier material and (ii) an excess of a labeled antibody to thyroxine binding globulin over endogenous thyroxine binding globulin, to form a complexed composite;
   (b) separating the complexed composite from any unbound labeled antibody;
   (c) measuring the amount of label associated with the complexed composite: and
   (d) determining a thyroxine uptake ratio of the sample serum by relating the measurement of step c) to a measurement of a reference serum.

2. A method as recited in claim 1 wherein the insoluble carrier material is a high surface area, insoluble material, in particulate form having an average particle size of from about 0.01 to about 10 microns in diameter.

3. A method as recited in claim 1 wherein the insoluble carrier material comprises paramagnetic particles.

4. A method as recited in claim 1 wherein the label is selected from the group consisting of enzymatic, flourogenic, radiometric, bioluminescent and chemiluminescent labels.

5. A method as recited in claim 4 wherein the label is a chemiluminescent label.

6. A method as recited in claim 5 wherein the chemiluminescent label is an acridinium ester.

7. A method as recited in claim 6 wherein the acridinium ester label is derived from 2', 6'-dimethyl-4'-(N-succinimidyloxycarbonyl)phenyl acridine-9-carboxylate.

8. A method as recited in claim 1 wherein the insoluble carrier material comprises paramagnetic particles and wherein the labeled antibody to thyroxine binding globulin is prepared from anti-thyroxine binding globulin antibody and an acridinium ester.

9. A method as recited in claim 8 wherein there are about 0.1 to 1.0 µg of thyroxine immobilized on the paramagnetic particles per 10 µl of the sample serum and wherein there are about 10 ng to about 100 ng of the labeled antibody to thyroxine binding globulin per 10 µl of the sample serum.

10. A method as recited in claim 9 wherein there are about 0.5 µg of thyroxine immobilized on the paramagnetic particles per 10 µl of sample serum and wherein there are about 50ng of the labeled antibody to thyroxine globulin per 10 µl of the sample serum.

11. A method as recited in claim 1 wherein step (d) is determined using the following equation:

$$T\text{-uptake ratio} = \frac{\text{measurement from reference serum}}{\text{measurement from sample serum}}$$

12. A method for determining the free thyroxine index of a sample serum which comprises:
   (a) determining the total T$_4$ of the sample serum;
   (b) determining the T-uptake ratio according to the method recited in claim 11; and
   (c) relating the determination of step (a) to the determination of step (b) to determine the free thyroxine index, by using the following equation:

$$FTI = \text{Total } T_4 \times \frac{T\text{-uptake ratio}}{100}$$

* * * * *